US010729811B2

(12) United States Patent
Rajamannan

(10) Patent No.: US 10,729,811 B2
(45) Date of Patent: Aug. 4, 2020

(54) METHODS FOR INHIBITING STENOSIS, OBSTRUCTION, OR CALCIFICATION OF A STENTED HEART VALVE OR BIOPROSTHESIS

(71) Applicant: CONCIEVALVE LLC, Minneapolis, MN (US)

(72) Inventor: Nalini M. Rajamannan, Chicago, IL (US)

(73) Assignee: CONCIEVALVE, LLC, Minneapolis, MN (US)

( * ) Notice: Subject to any disclaimer, the term of this patent is extended or adjusted under 35 U.S.C. 154(b) by 0 days.

(21) Appl. No.: 15/997,171

(22) Filed: Jun. 4, 2018

(65) Prior Publication Data

US 2018/0280573 A1 Oct. 4, 2018

Related U.S. Application Data

(60) Continuation of application No. 15/601,236, filed on May 22, 2017, now Pat. No. 10,058,630, which is a
(Continued)

(51) Int. Cl.
*A61F 2/24* (2006.01)
*A61L 27/36* (2006.01)
(Continued)

(52) U.S. Cl.
CPC ........ *A61L 27/3625* (2013.01); *A61F 2/2412* (2013.01); *A61K 9/0024* (2013.01);
(Continued)

(58) Field of Classification Search
CPC ........... A61L 27/3625; A61L 2300/416; A61F 2/2418; A61F 2/2412; A61F 2/24
See application file for complete search history.

(56) References Cited

U.S. PATENT DOCUMENTS 5,411,552 A * 5/1995 Andersen ............... A61F 2/2418
137/343
5,476,516 A 12/1995 Seifter et al.
(Continued)

FOREIGN PATENT DOCUMENTS

CN 101309653 A 11/2008
CN 101548916 A 10/2009
(Continued)

OTHER PUBLICATIONS

Cowell, S. Joanna, et al., "A Randomized Trial of Intensive Lipid-Lowering Therapy in Calcific Aortic Stenosis," The New England Journal of Medicine, 2005, vol. 352, No. 23, pp. 2389-2397.
(Continued)

*Primary Examiner* — Seema Mathew
(74) *Attorney, Agent, or Firm* — Fox Rothschild LLP

(57) ABSTRACT

Methods for inhibiting stenosis, obstruction and/or calcification of a heart valve following implantation in a vessel having a wall are disclosed. In one aspect the method includes providing a bioprosthetic heart valve mounted on an elastical stent; treating the bioprosthetic heart valve with a tissue fixative; coating the stent and the bioprosthetic valve with a coating composition including one or more therapeutic agents; implanting the bioprosthetic valve into the vessel in a diseased natural valve site; eluting the coating composition from the bioprosthetic valve; and inhibiting stenosis, obstruction and/or calcification of the bioprosthetic heart valve by preventing the attachment of stem cells to the bioprosthetic heart valve, the stem cells circulating external and proximate to the bioprosthetic heart valve by activating nitric oxide production (i) in the circulating stem cells, (ii) in an endothelial cell lining covering the bioprosthetic heart valve tissue, (iii) or both.

6 Claims, 7 Drawing Sheets

Related U.S. Application Data continuation-in-part of application No. 15/193,208, filed on Jun. 27, 2016, now abandoned, which is a division of application No. 14/263,438, filed on Apr. 28, 2014, now abandoned, which is a continuation-in-part of application No. 13/656,925, filed on Oct. 22, 2012, now abandoned, said application No. 15/601,236 is a continuation-in-part of application No. 14/687,479, filed on Apr. 15, 2015, now abandoned, which is a continuation-in-part of application No. 14/263,438, filed on Apr. 28, 2014, now abandoned, which is a continuation-in-part of application No. 13/656,925, filed on Oct. 22, 2012, now abandoned, said application No. 15/601,236 is a continuation-in-part of application No. 15/031,532, filed as application No. PCT/US2014/061745 on Oct. 22, 2014, now abandoned, which is a continuation-in-part of application No. 14/263,438, filed on Apr. 28, 2014, now abandoned, which is a continuation-in-part of application No. 13/656,925, filed on Oct. 22, 2012, now abandoned.

(51) Int. Cl.
| | |
|---|---|
| *A61L 27/54* | (2006.01) |
| *A61L 31/16* | (2006.01) |
| *A61K 9/00* | (2006.01) |
| *A61K 31/40* | (2006.01) |
| *A61L 31/14* | (2006.01) |
| *A61K 31/337* | (2006.01) |

(52) U.S. Cl.
CPC ............ *A61K 31/337* (2013.01); *A61K 31/40* (2013.01); *A61L 27/54* (2013.01); *A61L 31/14* (2013.01); *A61L 31/16* (2013.01); *A61F 2/2418* (2013.01); *A61F 2250/0067* (2013.01); *A61L 2300/204* (2013.01); *A61L 2300/21* (2013.01); *A61L 2300/258* (2013.01); *A61L 2300/416* (2013.01); *A61L 2300/606* (2013.01); *A61L 2400/02* (2013.01); *A61L 2430/20* (2013.01)

(56) References Cited

U.S. PATENT DOCUMENTS

| | | | |
|---|---|---|---|
| 6,517,571 B1* | 2/2003 | Brauker | A61F 2/06 623/1.13 |
| 6,534,538 B2 | 3/2003 | Rajamannan | |
| 6,660,260 B1 | 12/2003 | Rajamannan | |
| 7,261,732 B2 | 8/2007 | Justino | |
| 8,038,709 B2 | 10/2011 | Palasis et al. | |
| 8,530,414 B2* | 9/2013 | Davies | C07K 16/40 514/7.4 |
| 8,585,753 B2 | 11/2013 | Scanlon et al. | |
| 8,951,513 B2* | 2/2015 | Alt | B04B 5/0414 424/93.7 |
| 9,211,361 B2 | 12/2015 | Schankereli | |
| 9,744,265 B2 | 8/2017 | Schmuck et al. | |
| 9,878,068 B2* | 1/2018 | Davidson | A61L 27/507 |
| 10,077,319 B2* | 9/2018 | Celeste | A61K 38/26 |
| 2002/0159983 A1 | 10/2002 | Rajamannan | |
| 2002/0193336 A1 | 12/2002 | Elkins et al. | |
| 2003/0212454 A1 | 11/2003 | Scott et al. | |
| 2004/0024452 A1 | 2/2004 | Kruse et al. | |
| 2004/0186563 A1 | 9/2004 | Lobbi | |
| 2004/0210304 A1 | 10/2004 | Seguin et al. | |
| 2005/0154451 A1* | 7/2005 | Hezi-Yamit | A61F 2/82 623/1.42 |
| 2005/0244460 A1 | 11/2005 | Alferiev et al. | |
| 2005/0256588 A1 | 11/2005 | Sawa et al. | |
| 2005/0267560 A1 | 12/2005 | Bates | |
| 2006/0122692 A1 | 6/2006 | Gilad et al. | |
| 2006/0149367 A1 | 7/2006 | Sieracki | |
| 2006/0195180 A1 | 8/2006 | Kheradvar et al. | |
| 2006/0271171 A1 | 11/2006 | McQuinn et al. | |
| 2006/0286141 A1 | 12/2006 | Campbell | |
| 2006/0293745 A1 | 12/2006 | Carpentier et al. | |
| 2007/0059293 A1* | 3/2007 | Atala | A61L 27/3839 424/93.7 |
| 2007/0196423 A1 | 8/2007 | Ruane et al. | |
| 2007/0237802 A1 | 10/2007 | McKay | |
| 2008/0086205 A1* | 4/2008 | Gordy | A61L 27/34 623/2.42 |
| 2009/0048173 A1* | 2/2009 | Eisert | A61K 31/519 514/6.9 |
| 2009/0164005 A1* | 6/2009 | Dove | A61L 27/3604 623/2.13 |
| 2010/0030340 A1 | 2/2010 | Wolfinbarger, Jr. et al. | |
| 2011/0015252 A1* | 1/2011 | Fitzgerald | A61K 9/0019 514/44 A |
| 2011/0052621 A1* | 3/2011 | Champion | A61K 39/0005 424/193.1 |
| 2011/0137397 A1 | 6/2011 | Chau et al. | |
| 2011/0200563 A1 | 8/2011 | Vao | |
| 2011/0238167 A1 | 9/2011 | Dove et al. | |
| 2012/0183971 A1 | 7/2012 | Schussler | |
| 2013/0095167 A1 | 4/2013 | Warnke | |
| 2013/0197667 A1* | 8/2013 | Ingham | A61L 27/3625 623/23.72 |
| 2014/0094898 A1* | 4/2014 | Borck | A61L 27/34 623/1.15 |
| 2014/0100648 A1 | 4/2014 | Matheny | |
| 2014/0161821 A1 | 6/2014 | Udata | |
| 2014/0274964 A1 | 9/2014 | Gordon et al. | |
| 2014/0296166 A1 | 10/2014 | Lyles et al. | |
| 2015/0140002 A1* | 5/2015 | Baccara-Dinet | A61K 45/06 424/139.1 |
| 2015/0209813 A1 | 7/2015 | Sternberg et al. | |
| 2015/0231236 A1 | 8/2015 | Pordy et al. | |
| 2015/0306281 A1 | 10/2015 | Rajamannan | |
| 2016/0279085 A1 | 9/2016 | Martin et al. | |

FOREIGN PATENT DOCUMENTS

| | | |
|---|---|---|
| EP | 2703008 A1 | 3/2014 |
| JP | 2004-097810 A | 4/2004 |
| JP | 2008-541865 A | 11/2008 |
| JP | 2013-023499 A | 2/2013 |
| WO | WO-2001-82992 A1 | 11/2001 |
| WO | WO-0182992 A1 | 11/2001 |
| WO | WO-03020329 A1 | 3/2003 |
| WO | WO-2007-059253 A2 | 5/2007 |
| WO | WO-2008/043753 A2 | 4/2008 |
| WO | WO-2010-057177 A2 | 5/2010 |
| WO | WO-2012-002228 A1 | 1/2012 |
| WO | WO-2013-110393 A1 | 8/2013 |
| WO | WO-2014-179280 A1 | 11/2014 |
| WO | WO-2014/194168 A2 | 12/2014 |
| WO | WO-2015036512 A1 | 3/2015 |
| WO | WO-2015-061431 A1 | 4/2015 |
| WO | WO-2015073494 A1 | 5/2015 |

OTHER PUBLICATIONS

Giugliano, Robert P., et al., "Efficacy, safety, and tolerablility of a monoclonal antibody to proprotein convertase subtilisin/kexin type 9 in combination with a statin in patients with hypercholesterolaemia, (LAPLACE_TIMI 57): a randomised, placebo-controlled, close-ranging, phase 2 study." The Lancet, 2012, vol. 380, No. 9858, p. 2007-2017.

Wu, Bing, et al., "Paradoxical effects of statins on Aortic Valve Myofibroblasts and Osteoblasts Implication for End-Stage Valvular Heart Disease," Arteriosclerosis, Thrombosis, and Vascular Biology, 2005, vol. 25, No. 3, p. 592-597.

Yoshiaki Ohyama, Masahiko Kurabayashi, "Valvular Disease in Anti-Aging Science," Anti-Aging Science, 2012, vol. 4, No. 2, pp. 94-98. (Untranslated).

(56) References Cited

OTHER PUBLICATIONS

Japan Office Action, issued by the Japanese Patent Office, regarding corresponding patent application Serial No. JP 2017-553407; dated Jul. 18, 2018; 20 pages. (Translated).
Roth, Eli M., et al. "Atorvastatin with or without an Antibody to PCSK9 in Primary Hypercholesterolemia," New England Journal of Medicine, vol. 367, No. 20, Nov. 15, 2012; pp. 1891-1900.
Nikolov Igor G. et al., "Farnesyltransferase Inhibitor R115777 Protects Against Vascular Disease in Uremic Mice." Atherosclerosis, Elsevier, Amsterdam, NL; vol. 229, No. 1, Apr. 22, 2013, pp. 42-51.
Gian Paolo Ussia, et al "Dual Antiplatelet Therapy Versus Aspirin Alone in Patients Undergoing Transcatheter Aortic Valve Implantation," American Journal of Cardiology, Cahners Publishing Co., Newton, MA, USA; vol. 108, No. 12, Jul. 15, 2011; pp. 1772-1776.
Extended European Search Report, issued by the European Patent Office, regarding corresponding patent application Serial No. EP 16780828.6, dated Oct. 24, 2018, 13 pages.
J. Gustav Smith et al.; "Association of Low-Density Lipoprotein Cholesterol-Related Genetic Variants with Aortic Valve Calcium and Incident Aortic Stenosis," JAMA The Journal of American Medical Association; vo. 312, No. 17, Nov. 5, 2014; p. 1764. US.
Australian Examination Report No. 1, issued by the Australian Patent Office, regarding patent application Serial No. AU 2016248997, dated Apr. 9, 2018, 4 pages.
Australian Examination Report No. 2, issued by the Australian Patent Office, regarding patent application Serial No. AU 2016248997, dated Sep. 25, 2018, 3 pages.
Australian Examination Report No. 3, issued by the Australian Patent Office, regarding patent application Serial No. AU 2016248997, dated Dec. 5, 2018, 8 pages.
Leskelä, et al., "Calcification and Cellularity in Human Aortic Heart Valve Tissue Determine the Differentiation of Bone-Marrow-Derived Cells," Journal of Molecular and Cellular Cardiology (2006), vol. 41, No. 4, pp. 642-649.
Li, et al., "Intensive Statin Therapy: A Favorable Adjunct to the Improvement of Small-Diameter Vascular Grafts," Angiology (2010), vol. 61, No. 5, pp. 427-436.
Rajamannan, N., "Atorvastatin Attenuates Aortic Valve Disease via a Tissue Stem Cell Niche," Arteriosclerosis, Thrombosis and Vascular Biology (2010) vol. 29, No. 7, p. e114, Abstract p. 564.
Osman, et al., "Role of Human Valve Interstitial Cells in Valve Calcification and Their Response to Atorvastatin," Circulation (2006), vol. 114, Supplement I, pp. I-547-I-552.
Lorusso et al., "Atorvastatin Attenuates Post-Implant Tissue Degeneration of Cardiac Prosthetic Valve Bovine Pericardial Tissue in a Subcutaneous Animal Model," International Journal of Cardiology (2010), vol. 141, No. 1, pp. 68-74.
Rajamannan, et al., "Atorvastatin Attenuates Bioprosthetic Heart Valve Calcification in a Rabbit Model Via a Stem Cell Mediated Mechanism," Journal of the American College of Cardiology (2008), vol. 51, No. 10, Suppl. A, p. A277, Abstract 816-7.
Rajamannan, N, "Cellular Mechanisms of Bioprosthetic Aortic Valve Calcification the Role of Statins", European Heart Journal Cardiovascular Imaging (2012), vol. 13, Suppl. 1, p. i49, Abstract P. 374.
Australian Examination Report No. 1, issued by the Australian Patent Office, regarding corresponding patent application Serial No. AU 2017291139, dated Feb. 14, 2019; 5 pages.

International Search Report and Written Opinion, issued by the ISA/US Receiving Office, regarding corresponding patent application Serial No. PCT/US2013/066142; dated Jan. 9, 2014, 10 pages. USA.
International Search Report and Written Opinion, issued by the ISA/US Receiving Office, regarding corresponding patent application Serial No. PCT/US2014/061745; dated Feb. 5, 2015, 7 pages. USA.
International Search Report and Written Opinion, issued by the ISA/US Receiving Office, regarding corresponding patent application Serial No. PCT/US2016/027738, dated Aug. 26, 2016, 9 pages. USA.
International Search Report and Written Opinion, issued by the ISA/U.S. Receiving Office, regarding coresponding patent application Serial No. PCT/US2017/033792, dated Aug. 28, 2017, 13 pages. USA.
First Office Action, issued by the State Intellectual Property Office of P.R. China, regarding corresponding patent application Serial No. 201480065322.2; dated Jan. 25, 2017, 7 pages. P.R. China.
Extended European Search Report (EESR), issued by the European Patent Office, in corresponding patent application Serial No. EP 14855873, dated Jun. 2, 2017, 9 pages; EPO.
Japan Official Action, issued by the Japanese Patent Office, regarding corresponding patent application Serial No. JP 2016-526201; dated Apr. 18, 2017; 7 pages. Japan.
Rajamannan, Nalini M., et al.; Abstracts—Valvular Heart Disease, ACC Oral Contributions, "Emerging Insights Into the Pathogenesis of Valvular Heart Disease"; "Atorvastatin Attenuates Bioprosthetic Heart Valve Calcification in a Rabbit Model via a Stem Cell Mediated Mechanism"; published in JACC, Mar. 11, 2008; p. A277; USA.
Kieran, MW et al.;"Phase I and Pharmacokinetic Study of the Oral Farnesyltransferase Inhibitor Lonafarnib Administered Twice Daily to Pediatric Patients With Advanced Central Nervous System Tumors Using a Modified Continuous Reassessment Method: A Pediatric Brain Tumor Consortium Study"; Jul. 20, 2007. Journal of Clinical Oncology. vol. 25; No. 21; p. 3137.
American College of Cardiology; "Clopidogrel, Prasugrel, Ticagrelor," Mar. 13, 2012., pp. 1 and 3-4. Accessed <http://www.acc.orci/latestincardiology/> articles/2012/03/13/15/07/clopidogrel.
European Office Action, issued by the European Patent Office, regarding corresponding patent application Serial No. EP16780828. 6; dated Jun. 25, 2019; 10 pages.
Pahan K: "Lipid-lowering drugs", Cellular and Molecular Life Sciences, Birkhauser-Verlag, BA, vol. 63, No. 10, Mar. 29, 2006 (Mar. 29, 2006), pp. 1165-1178.
Japan Office Action, issued by the Japanese Patent Office, regarding corresponding patent application Serial No. JP 2017-553407; dated Mar. 25, 2019; 5 pages. (Translated).
Bogle, Richard G. et. al., "Identification of Inhibitors of Nitric Oxide Synthase That Do Not Interact With the Endotheilial Cell L-arginine Transporter", British Journal of Pharmacology, 1992, vol. 105, pp. 768-770.
Japan Official Action, issued by the Japanese Patent Office, regarding corresponding patent application Serial No. JP 2019-519962; dated Dec. 4, 2019; 14 pages.
Shimamura et al., Jinko Zoki, 2011, vol. 40, No. 3, pp. 161-164, 4 pages (no translation).

\* cited by examiner

| TABLE 2 | CONTROL | CHOLESTEROL | CHOL + ATORV |
|---|---|---|---|
| CHOLESTEROL (mg/dl) | 18 ± 7 | 1846.3 ± 525.3* | 842 ± 152.1** |
| TRIGLYCERIDES (mg/dl) | 102.3 ± 16.9 | 323.25 ± 274.6* | 97 ± 27.1** |
| HDL (mg/dl) | 4.6 ± 5.1 | 21.3 ± 7.5* | 24.7 ± 16.7 |
| hsCRP (mg/dl) | 0.24 ± 0.1 | 13.6 ± 19.7* | 7.82 ± 8.7** |
| CKIT | 681 ± 618 | 978 ± 1217 | 302 ± 290** |
| OPN | 1373 ± 1216 | 1662 ± 1491 | 1483 ± 1501 |
| CYCLIN | 1461 ± 1339 | 2988 ± 3451* | 984 ± 970** |
| SOX9 | 580 ± 459 | 910 ± 554* | 168 ± 102** |
| GAPDH | 2233 ± 2887 | 2553 ± 3013 | 2456 ± 3158 |
| MORPHOMETRIC MEASUREMENT OF ATHEROSCLEROSIS BURDEN | ++ | +++++ | +** |

Fig. 7

METHODS FOR INHIBITING STENOSIS, OBSTRUCTION, OR CALCIFICATION OF A STENTED HEART VALVE OR BIOPROSTHESIS

CROSS REFERENCE TO RELATED APPLICATIONS

This application is a continuation of U.S. application Ser. No. 15/601,236, filed on May 22, 2017, pending; which is a continuation-in-part of U.S. application Ser. No. 15/193,208, filed on Jun. 27, 2016, abandoned; which is divisional of U.S. application Ser. No. 14/263,438 filed on Apr. 28, 2014, abandoned; which is a continuation-in-part of U.S. application Ser. No. 13/656,925, filed on Oct. 22, 2012, abandoned; wherein U.S. application Ser. No. 15/601,236 is also a continuation-in-part of U.S. application Ser. No. 14/687,479, filed on Apr. 15, 2015, abandoned; which is a continuation-in-part of U.S. application Ser. No. 14/263,438 filed on Apr. 28, 2014, abandoned; which is a continuation-in-part of U.S. application Ser. No. 13/656,925, filed on Oct. 22, 2012, abandoned; wherein U.S. application Ser. No. 15/601,236 is also a continuation-in-part of U.S. application Ser. No. 15/031,532, filed on Apr. 22, 2016, abandoned; which is a 371(c) national stage application claiming priority to International patent application Ser. No. PCT/US2014/061745, filed on Oct. 22, 2014, which is a continuation-in-part of U.S. application Ser. No. 14/263,438 filed on Apr. 28, 2014, abandoned; which is a continuation-in-part of U.S. application Ser. No. 13/656,925, filed on Oct. 22, 2012, abandoned; the entireties of the foregoing hereby being incorporated by reference.

FIELD OF THE INVENTION

The invention relates to methods for inhibiting stenosis, obstruction, or calcification of heart valves and heart valve prostheses.

BACKGROUND OF THE INVENTION

The heart is a hollow, muscular organ that circulates blood throughout an organism's body by contracting rhythmically. In mammals, the heart has four-chambers situated such that the right atrium and ventricle are completely separated from the left atrium and ventricle. Normally, blood flows from systemic veins to the right atrium, and then to the right ventricle from which it is driven to the lungs via the pulmonary artery. Upon return from the lungs, the blood enters the left atrium, and then flows to the left ventricle from which it is driven into the systemic arteries.

Four main heart valves prevent the backflow of blood during the rhythmic contractions: the tricuspid, pulmonary, mitral, and aortic valves. The tricuspid valve separates the right atrium and right ventricle, the pulmonary valve separates the right atrium and pulmonary artery, the mitral valve separates the left atrium and left ventricle, and the aortic valve separates the left ventricle and aorta. Generally, patients having an abnormality of a heart valve are characterized as having valvular heart disease.

One way a heart valve can malfunction is by failing to open properly due to stenosis, requiring replacement of the valve by surgical or transcutaneous arterial means. Replacement valves are typically bioprosthetic valves made from valves of other animals, such as pig or cow. Unfortunately, over time, the replacement valves themselves are susceptible to problems such as stenosis, obstruction and calcification.

For years cardiac calcification was thought to be a passive degenerative phenomenon. Rajamannan's work in U.S. Pat. Appln. No. 2002/0159983 first attempted, unsuccessfully, to address the issue of stenosis and calcification of diseased heart valves. Rajamannan discloses a method for inhibiting stenosis, obstruction or calcification of heart valve tissue having live, non-fixed heart valve cells that contain an exogenous nucleic acid that encodes or activates endothelial nitric oxide synthase—a polypeptide having nitric oxide synthase activity. It was thought at the time that nitric oxide would stop the calcification of the live tissue before it was processed using glutaraldehyde. Rajamannan used a virus (e.g. retrovirus, adenovirus, or herpes virus) to introduce the exogenous nucleic acid (eNOS) by injection into a live cell of the heart valve (human or porcine—in vivo or in vitro) such that the polypeptide—endothelial nitric oxide synthase—is expressed. It was thought that the cell would make excessive amount of nitric oxide synthase that would stop calcification. Rajamannan also discloses administering an inhibitor of hydroxymethylglutaryl coA reductase activity, such as pravastatin, atorvastatin, simvastatin or lovastatin orally to the mammal and/or bathing the cells with bovine serum containing the foregoing. After the foregoing treatment, the human or porcine heart valve was fixed with glutaraldehyde. As noted above, this technique was unsuccessful.

What is needed are new methods and systems that inhibit the formation of stenosis, obstruction, and/or calcification of heart valves and bioprosthetic heart valves.

BRIEF SUMMARY OF THE INVENTION

The heart valve and method in accordance with the invention addresses the shortcomings with conventional bioprosthetic, surgical and mechanical heart valves.

In one aspect the method for inhibiting stenosis, obstruction and/or calcification of a heart valve following implantation in a vessel having a wall includes providing a bioprosthetic heart valve comprising tissue having one or more cusps, the bioprosthetic heart valve mounted on an elastical stent for replacement of a natural diseased valve; treating the bioprosthetic heart valve with a tissue fixative; coating the stent, one or more cusps, or both with a coating composition comprising one or more therapeutic agents; implanting the bioprosthetic valve into the vessel in a diseased natural valve site; eluting the coating composition from the elastical stent, one or more cusps, or both; inhibiting stenosis, obstruction and/or calcification of the bioprosthetic heart valve by preventing the attachment of stem cells to the bioprosthetic heart valve, the stem cells circulating external and proximate to the bioprosthetic heart valve, elastical stent or both by activating nitric oxide production (i) in the circulating stem cells, (ii) in an endothelial cell lining covering the bioprosthetic heart valve tissue, (iii) or both.

In another aspect of the invention, the method the stem cells are cKit positive stem cells SCA1 cells, COP cells, mesenchymal stem cells and combinations of the foregoing.

In another aspect of the invention, the method includes treating the bioprosthetic heart valve tissue with an eNOS activator selected from Atorvastatin, Rosuvastatin, Pravastatin, Mevastatin, Fluvastatin, Simvastatin, Lovastatin, L-Arginine, citrulline, NADPH, acetylcholine, histamine, arginine vasopressin, norepinephrine, epinephrine, bradykinin, adenosine di,triphosphate, 5-Hydroxytrptamine, thrombin, insulin, glucocorticoids, salicylates, L-NMMA, L-NAME, nitroglycerine, isosorbide dinitrate, isosorbide 5-mononitrate, amyl nitrite, nicorandil, tetrahydrobiopterin, Zetia and combinations of the foregoing.

In another aspect of the invention, the coating composition includes one or more of (i) an anti-proliferative agent; (ii) an inhibitor of extracellular production; (iii) an inhibitor of osteoblastogenesis; and (iv) combinations of the foregoing for inhibiting bone formation in an osteoblast cell originating from the stem cells.

In another aspect of the invention the anti-proliferative agent is paclitaxel, sirolimus, biolimus, everolimus and combinations of the foregoing.

In another aspect of the invention the inhibitor of extracellular production is an anti-farnysltransferase inhibitor, an anti-palmitoylation inhibitor or both.

In another aspect of the invention the anti-famysltransferase inhibitor and/or the anti-palmitoylation inhibitor include Lonafarnib, Zarnestra R115777, FTI SCH66336, STI571, FLT-3 Inhibitor, Proteasome Inhibitor, MAPK Inhibitor, BMS-214662, Type I non-lipid inhibitors of protein palmitoylation, farnesyl-peptide palmitoylation or Type 2 inhibitors myristoyl-peptide palmitoylation, palmitoylation acyltransferase inhibitors, lipid based palmitoylation inhibitors including 2-bromopalmitoyl (2BP), tunicamycin, cerulnin and combinations of the foregoing.

In another aspect of the invention the inhibitor of osteoblastogenesis includes anti-osteoporotic agents such as bisphosphonate drugs including Alendronate, Risedronate, Zoledronic acid, Etidronate, Ibandronate, Pamidronate, Tiludronate, Denosumab antibody, Calcitonin-Calcimare, Miacalcin, Forteo teriparatide, raloxfine (Evista) and combinations of the foregoing.

In another aspect of the invention an oral dosage of eNOS activators are administered to a patient. The oral dosages include 10 mg to 80 mg per day of Atorvastatin; 10 mg to 40 mg Simvastatin per day; 5 mg to 40 mg Rosuvastatin per day; 10 mg to 40 mg Pravastatin per day; 1 mg to 4 mg Pitavastatin per day; 10 mg Zetia per day and combinations of the foregoing.

In another aspect of the invention an oral dosage of the anti-famysltransferase inhibitor, the anti-palmitoylation inhibitor or both is administered to a patient. The dosages may include Lonafarnib in a dosage of 115 mg/m2 dose with a range from 115 mg/m2 to 150 mg/m2, in combination with an effective amount of Zetia of 10 mg.

In another aspect of the invention, an effective amount of a PCSK9 inhibitor is administered to a patient by intramuscular or subcutaneous injection. An initial dose of the PCSK9 inhibitor may be from 0.25 mg/kg to 1.5 mg/kg; from 0.5 mg/kg to 1 mg/kg.

In another aspect of the invention an effective amount of the PCSK9 inhibitor is Alirocumab 75-150 mg every 2 to 4 weeks, Evolocumab 140 mg every 2 weeks or monthly and combinations of the foregoing.

BRIEF DESCRIPTION OF THE DRAWINGS

For a better understanding of the invention, and to show how the same may be carried into effect, reference will now be made, by way of example, to the accompanying drawings, in which:

FIG. 7 is a table setting forth the real-time polymerase chain reaction (RTPCR) results from the pericardial valves removed from the rabbit studies.

DETAILED DESCRIPTION OF THE INVENTION

Figure 1:
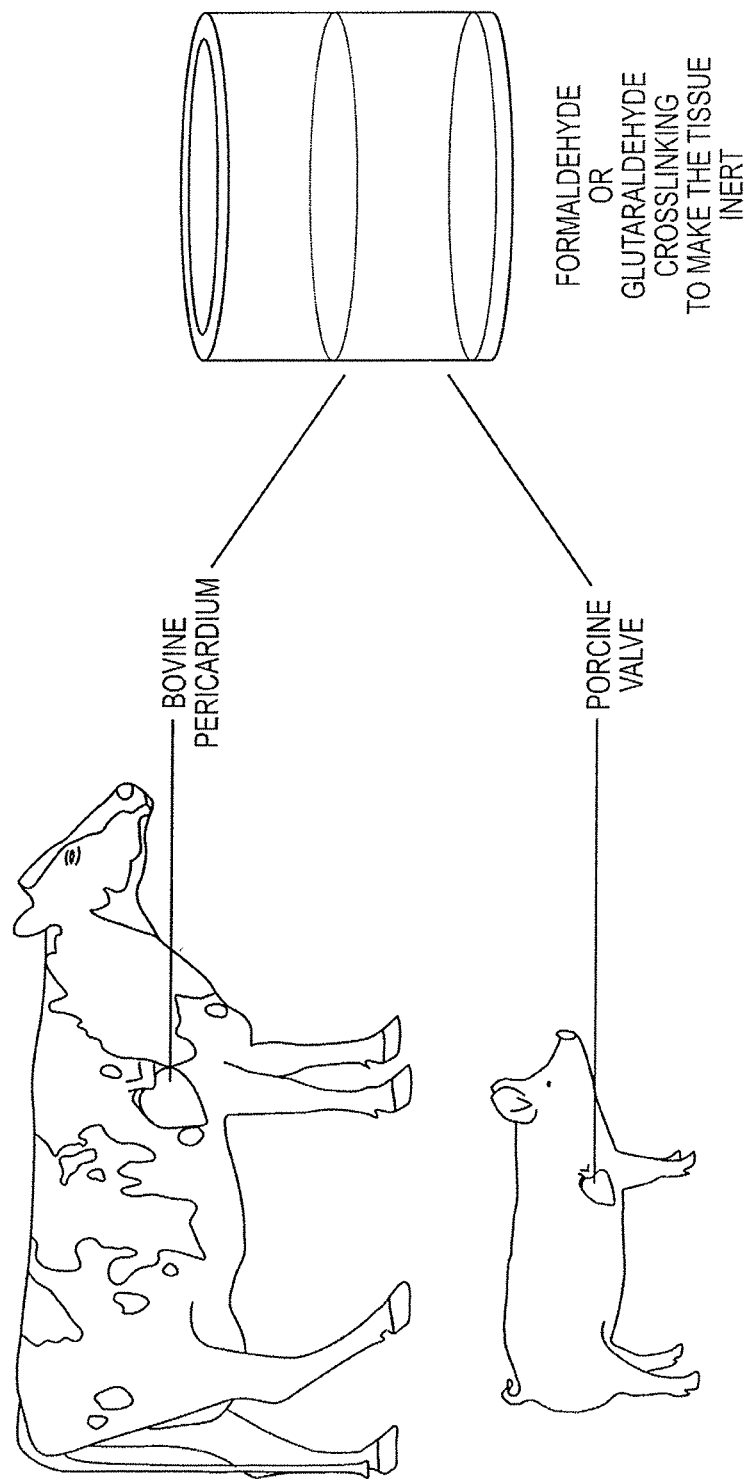
FIG. 1 is an illustration of the commercial process of obtaining a heart valve from a cow or pig and fixing it with glutaraldehyde to make the tissue inert and placing the tissue into a stented valve or surgical replacement valve.

The invention provides a method for inhibiting stenosis, obstruction, and/or calcification of a valve leaflets and valve tissue in a stented bioprosthetic heart valve 11 or a surgical replacement valve 10 with or without a sewing ring 12, following fixation of the valve and subsequent implantation of the valve in a patient in need thereof. The invention also provides a method for inhibiting stenosis, obstruction, and/ or calcification of a mechanical heart valve 14 having a Gortex lining 16 surrounding the sewing ring 18 of the mechanical heart valve.

As used herein, the term "stenosis" refers to the narrowing of a heart valve that could block or obstruct blood flow from the heart and cause a back-up of flow and pressure in the heart. Valve stenosis may result from various causes, including, but not limited to, scarring due to disease, such as rheumatic fever; progressive calcification; progressive wear and tear; among others. This is important not for the stented treatment but for the valve—is this flowing well with the rest of the patent.

As used herein, the term "valve" may refer to any of the four main heart valves that prevent the backflow of blood during the rhythmic contractions. The four main heart valves are the tricuspid, pulmonary, mitral, and aortic valves. The tricuspid valve separates the right atrium and right ventricle, the pulmonary valve separates the right atrium and pulmonary artery, the mitral valve separates the left atrium and left ventricle, and the aortic valve separates the left ventricle and aorta. Thus, in one aspect, the bioprosthetic valve and the diseased valve may be an aortic valve, pulmonary valve, tricuspid valve, or mitral valve.

As used herein, the term "bioprosthetic valve" is a stented tissue heart valve and may refer to a device used to replace or supplement a heart valve that is defective, malfunctioning, or missing. Examples of bioprosthetic valve prostheses include, but are not limited to, Edwards Sapien 1 Transcatheter Heart Valve, Edwards Sapien 2 Transcatheter Heart Valve, Edwards Sapien 3 Transcatheter Heart Valve, and all other variations of the Edwards Sapien Transcatheter valves, including but not limited to Edwards Sapien XT Transcatheter Heart Valve, Boston Scientific Lotus Edge Transcatheter Heart Valve and all variations of the Lotus Valve, Medtronic Core Valve Transcatheter Valve and Medtronic Core Valve Evolut R Transcatheter Valve, Melody Transcatheter Pulmonary Valve Therapy and all variations thereof.

Generally, bioprosthetic comprise a tissue valve having one or more cusps and the valve is mounted on a frame or stent, both of which are typically elastical. As used herein, the term "elastical" means that the device is capable of flexing, collapsing, expanding, or a combination thereof. The cusps of the valve are generally made from tissue of mammals such as, without limitation, pigs (porcine), cows (bovine), horses, sheep, goats, monkeys, and humans.

As used herein a "surgical heart valve" is one harvested from pigs or cows comprising only tissue and a sewing ring. The surgical heart valve is typically stentless. Non-limiting examples of surgical heart valves include ATS 3F Aortic Bioprosthesis, Carpentier-Edwards PERIMOUNT Magna Ease Aortic Heart Valve, Carpentier-Edwards PERIMOUNT Magna Aortic Heart Valve, Carpentier-Edwards PERIMOUNT Magna Mitral Heart Valve, Carpentier-Edwards PERIMOUNT Aortic Heart Valve, Carpentier-Edwards PERIMOUNT Plus Mitral Heart Valve, Carpentier-Edwards PERIMOUNT Theon Aortic Heart Valve, Carpentier-Edwards PERIMOUNT Theon Mitral Replacement System, Carpentier-Edwards Aortic Porcine Bioprosthesis, Carpentier-Edwards Duraflex Low Pressure Porcine Mitral Bioprosthesis, Carpentier-Edwards Duraflex mitral bioprosthesis (porcine), Carpentier-Edwards Mitral Porcine Bioprosthesis, Carpentier-Edwards S.A.V. Aortic Porcine Bioprosthesis, Edwards Prima Plus Stentless Bioprosthesis, Medtronic, Freestyle® Aortic Root Bioprosthesis, Hancock® II Stented Bioprosthesis, Hancock II Ultra® Bioprosthesis, Mosaic® Bioprosthesic, Mosaic Ultra® Bioprosthesis, St. Jude Medical, Biocor®, Biocor™ Supra, Biocor® Pericardia, Biocor™ Stentless, Epic™, Epic Supra™, Toronto Stentless Porcine Valve (SPVO), Toronto SPV II®, Trifecta, Sorin Group, Mitroflow Aortic Pericardial Valve®, Cryolife, Cryolife aortic Valve® Cryolife pulmonic Valve®, Cryolife-O'Brien stentless aortic xenograft Valve®Contegra Pulmonary Valve Conduit, Epic Stented Tissue Valve with Linx AC Technology, Aortic and Mitral Valves; Trifecta Valve with Guide Technology, Aortic and Mitral Valves.

As used herein a "mechanical heart valve" is one which is typically manufactured from a biocompatible material such as pyrolytic carbon. Non-limiting examples of mechanical heart valves include the SJM Regent Heart Valve, Mitral and Aortic Position; and the Starr-Edwards Valve, Mitral and Aortic Valves; Smeloff Cutler Valve, Mitral and Aortic Valves; Caged Ball Valve, Mitral and Aortic Valves; tilting disk valve, Mitral and Aortic Valves; bileaflet valve, Mitral and Aortic Valves; Bjork-Shiley Valve, Mitral and Aortic Valves; Medtronic Hall Heart Valve, Mitral and Aortic Valves, Annuloplasty Rings including the Physio I and Physio II, Duran AnCore Ring and Band, CG Future Composite Ring and Band, Profile 3D Ring, Open Pivot Mechanical Heart Valve, Medtroinc Open Pivot Aortic Valved Graft, Simulus Adjustable Annuloplasty System, Simulus Flexible Annuloplasty System, Simulus Semi-Rigid Annuloplasty System, Amplatzer Devices including but not limited to Patent Foramen Ovale, Ventricular Septal Closure Device, Atrial Septal Defect Device, Patent Ductus Arteriosus Device, and CryoLife On-X Valves, including but not limited to Aortic Heart Valve with Conform-A Sewing Ring, Aortic Heart Valve with Anatomic Sewing Ring, Aortic Heart Valve with Standard Sewing Ring, Mitral Heart Valve with Standard Sewing Ring, Mitral Heart Valve with Conform-X sewing Ring, Ascending Aortic Prosthesis.

Referring now to FIG. 1 two types of materials used for bioprosthetic heart valves, bovine pericardial and/or porcine aortic valve cusps, in surgical valve replacement versus transcutaneous valve replacement of native diseased valves are shown. The structural elements of the biomaterial and the modification of the tissue prior to placement in the sewing ring and or the surgical stent is a routine tissue preparation pretreatment called fixation by using aldehyde solutions to cause a cross linking of the tissue making it non-viable or inert, as shown in FIG. 1. "Fixation" of the tissue is performed using various concentrations of glutaraldehyde or formaldehyde. This pretreatment is performed to improve tissue durability using glutaraldehyde or formaldehyde as cross-linking agents.

After the valve leaflet, either bovine pericardial and or porcine aortic, is treated with glutaraldehyde or formaldehyde fixation and attached to the sewing ring and/or stent it is then placed in the human body to replace the diseased valve in one of two ways. The surgical approach involves opening the chest cavity to replace the diseased valve. The transcutaneous approach involves positioning the bioprosthetic valve on a catheter and threading it through an artery until the bioprosthetic valve reaches the diseased valve site where the diseased valve is replaced with the bioprosthetic valve using techniques known to those of skill in the art. A transapical approach may also be used wherein the bioprosthetic valve is introduced into the diseased valve site through the apex of the heart using techniques known to those of skill in the art.

Figure 2C:
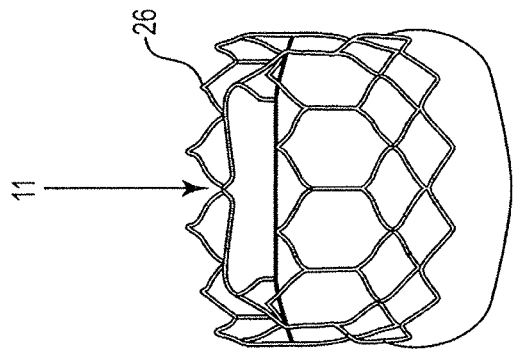
FIG. 2C is a perspective view of a transcutaneous, stented bioprosthetic heart valve.
Figure 2B:
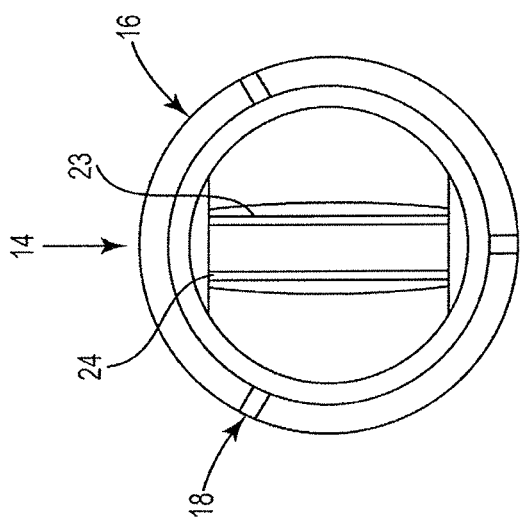
FIG. 2B is a top view of a mechanical heart valve having a Gortex covering on the sewing ring.
Figure 2A:
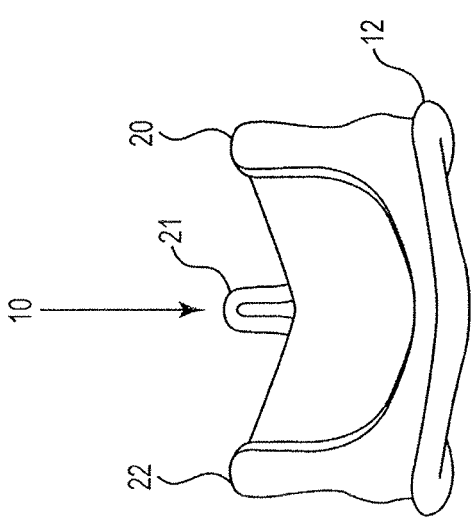
FIG. 2A is a perspective view of a bioprosthetic surgical heart valve with a sewing ring covered with tissue.

Referring now to FIGS. 2A-2C, the three different types of heart valves are illustrated. FIG. 2A depicts a bioprosthetic surgical heart valve 10 having three leaflets 20, 21, 22 and a sewing ring 12 covered by tissue. FIG. 2B depicts a mechanical heart valve 14 having two mechanical leaflets 23, 24. A mechanical heart valve is placed surgically using the open-chest procedure. While mechanical heart valves 14 do not use tissue for the leaflets, the valve structure itself 14, 23, 24 as well as the Gortex lining 16 covering the sewing ring 18 of mechanical heart valves may also be at risk for calcification. FIG. 2C depicts a bioprosthetic heart valve 11 mounted on stent 26. Stented bioprosthetic valves are typically placed transcutaneously through an artery and may also be placed transapically.

Figure 3:
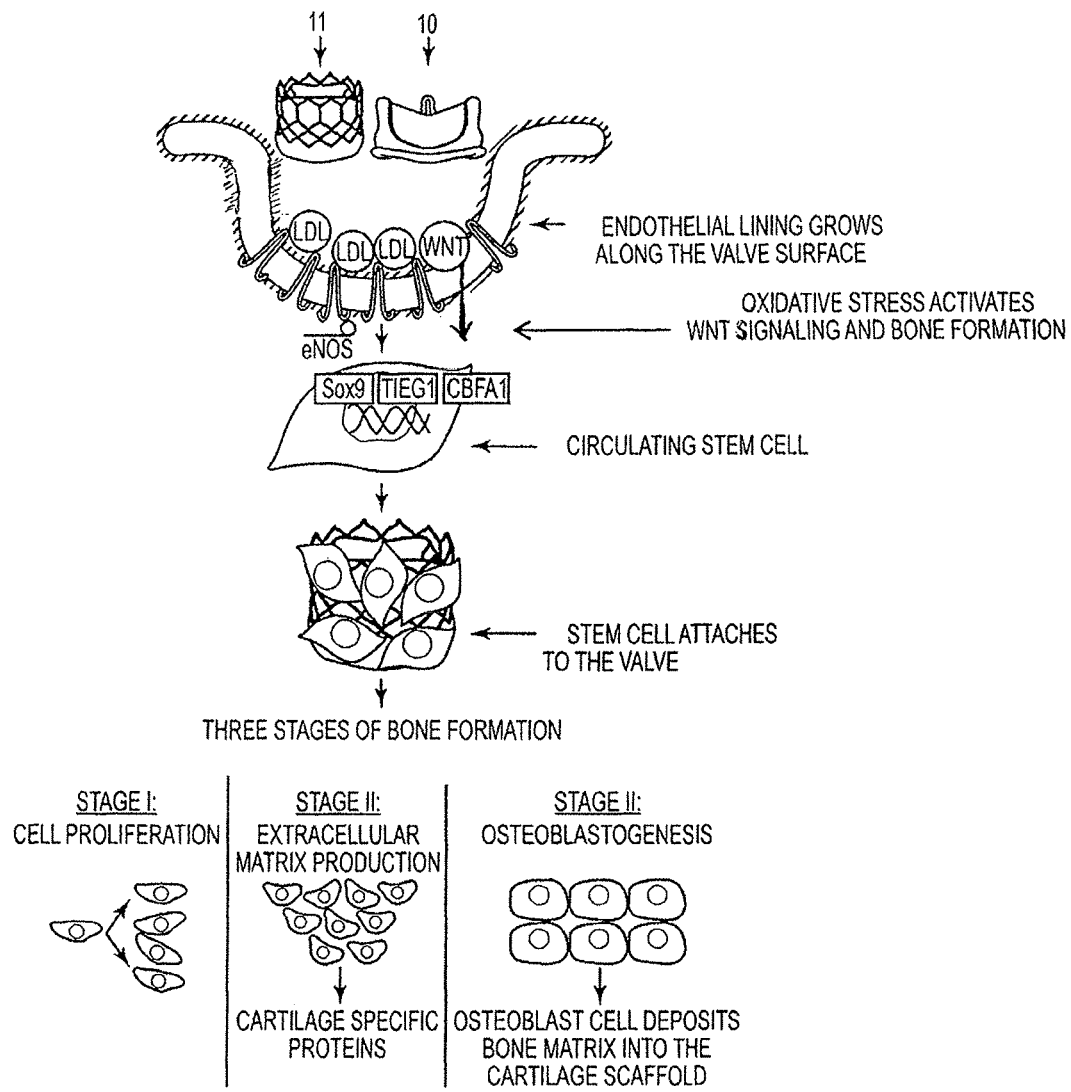
FIG. 3 illustrates the cellular origins of cardiac calcification and the three stages of bone formation on heart valves.
Figure 6:
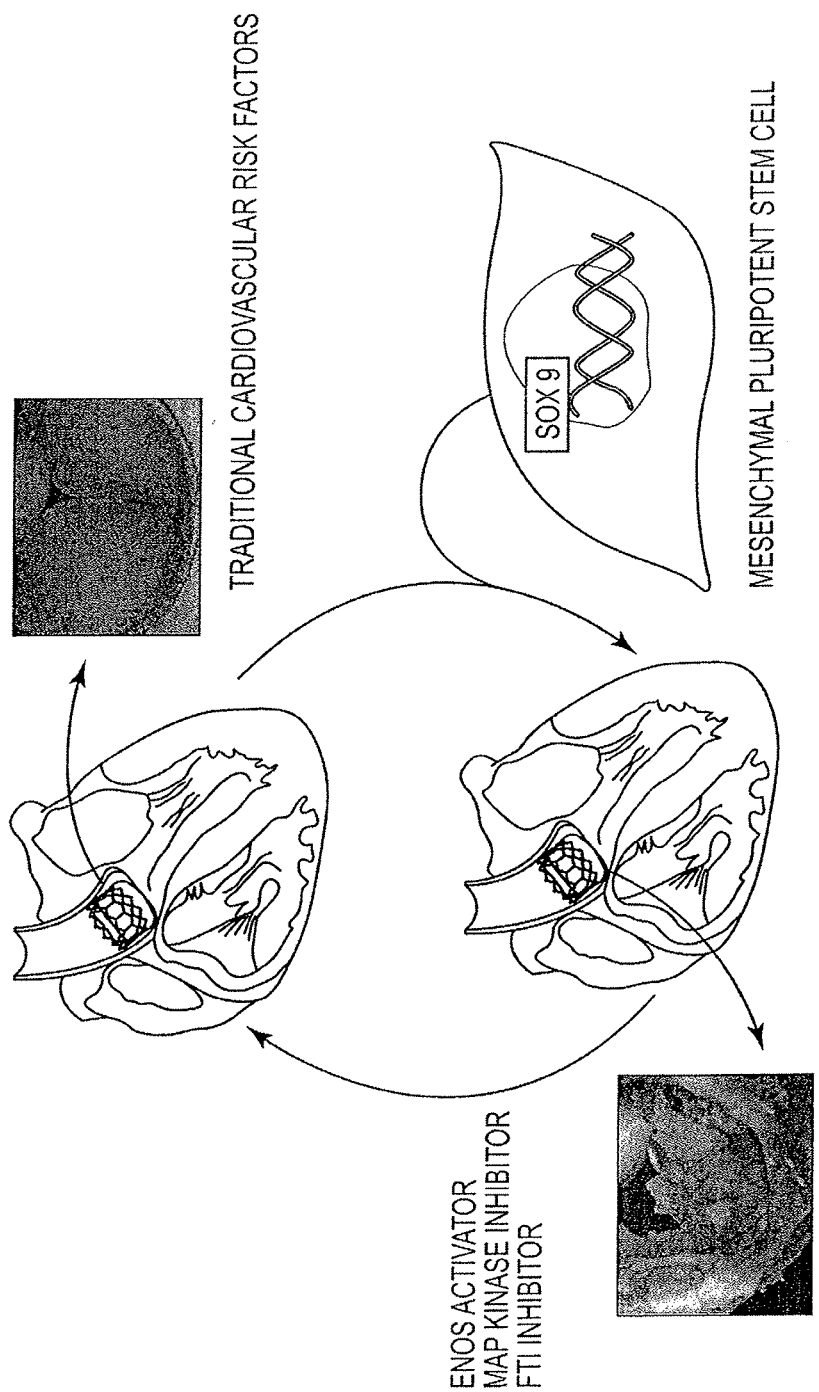
FIG. 6 illustrates the mechanism for bioprosthetic valve calcification.

In order to understand the method in accordance with the invention of inhibiting calcification, it is important to understand the mechanism of calcification, which is illustrated in FIGS. 3 and 6. As the valve is placed in the heart, either aortic, pulmonic, tricuspid and or mitral position in the heart, the heart produces an endothelial lining over the entire valve surface area including the leaflets, stent and the sewing ring during the several weeks following implantation and in the case of mechanical valves over the Gortex. Over time, exposure to stress elements such as high cholesterol, high blood pressure (hypertension), diabetes, smoking, and high levels of C-reactive protein cause the endothelial lining to decrease the eNOS function of the endothelial nitric oxide synthase gene and decrease the production of nitric oxide by the endothelial lining. Less nitric oxide production results in (i) the release of Wnt from the endothelial cells and (ii) the endothelial cells becoming "sticky" due to the decrease in production of nitric oxide. The release of Wnt in turn activates the Wnt cascade in circulating stem cells. Because the endothelial cells are "sticky" stem cells, cKIT positive cells, SCA1, circulating osteogenic precursor cells, mesenenchymal circulating stem cells, and combinations of the foregoing, attach to the abnormal endothelial lining that has grown on the valve. The release of Wnt and the activation of the Wnt cascade in the foregoing cells triggers the three stages of bone Ruination, namely cell proliferation, extracellular matrix production of cartilage specific proteins and osteoblastogenesis wherein the stem cells becomes an osteoblast cell that deposits bone matrix (calcium and phosphate) into the cartilage scaffold where the calcium and phosphate bind to the bone matrix. This bone matrix or calcification covers the bioprosthetic valve like a "shell," which is calcification and represents bone formation.

The present inventor tested the hypothesis that bioprosthetic valve calcification is a stem cell mediated atherosclerotic process. A model of prosthetic valve calcification for stem cell markers were tested. Normal bioprosthetic valves were implanted subcutaneously in rabbits (n=10) control, (n=10) 0.5% Cholesterol diet and (n=10) 0.5% Cholesterol+ Atorvastatin for three months to analyze for atherosclerotic bone formation. The bioprosthetic valve tissue explanted from the rabbits fed the cholesterol diets demonstrated severe atherosclerosis with islands of stem cell positive for ckit, macrophage, and osteopontin expression. Control valves demonstrated a mild increase in the markers. Atorvastatin treated valves had no evidence of stem markers or atherosclerosis (p<0.05). Bioprosthetic valve calcification is a mesenchymal ckit mediated atherosclerotic calcification process, which is attenuated by atorvastatin. These experimental data have implications for future therapy of patients with bioprosthetic valve to slow the progression of valve calcification.

Calcific aortic stenosis is the most common indication for surgical valve replacement in the United States and Europe. Currently, mechanical versus bioprosthetic heart valves are the two options for valve replacement. The choice of valve depends on patient characteristics at the time of surgery. Bioprosthetic heart valves have decreased risk of thrombosis, therefore decreasing the need for anticoagulation. Therefore, these are the valves of choice, in patients who are older than 75 years of age or who have contraindications to long-term anticoagulation, despite their limited long-term durability. A recent study demonstrated the expression of bone proteins in human aortic valve allografts setting the foundation for this disease process. It is estimated that 20-30% of implanted bioprosthetic heart valves will have some degree of hemodynamic dysfunction at 10 years. For years, the mechanisms of valve degeneration, was thought to be due to a passive process. However, recent studies have demonstrated risk factors for bioprosthetic valve calcification that are similar to vascular atherosclerosis. Furthermore, recent pathologic studies, have clearly shown that an inflammatory reaction develops in these calcifying bioprostheses which includes lipid deposits, inflammatory cell infiltration, and bone matrix proteins expression. These findings parallel a similar histopathologic lesion found in native calcific aortic valve disease.

To study the mechanism by which bioprosthetic heart valves calcify, this study tested a hypothesis that bioprosthetic valve calcification occurs secondary to a stem cell mediated atherosclerotic process. If atherosclerotic risk factors are independently associated with the development of bioprosthetic valve deterioration, then experimental models of atherosclerosis may provide a method to test the development of bioprosthetic valvular heart disease.

This study evaluated surgically implanted bovine pericardial valves in a rabbit model of hypercholesterolemia to determine if a similar atherosclerotic lesion develops along the surface of the implanted valve. To test the hypothesis that mesenchymal cKit positive stem cells home to the valves in the presence of inflammation. Finally, the study sought to determine if atorvastatin attenuates this atherosclerotic process in the experimental model.

Figure 4:
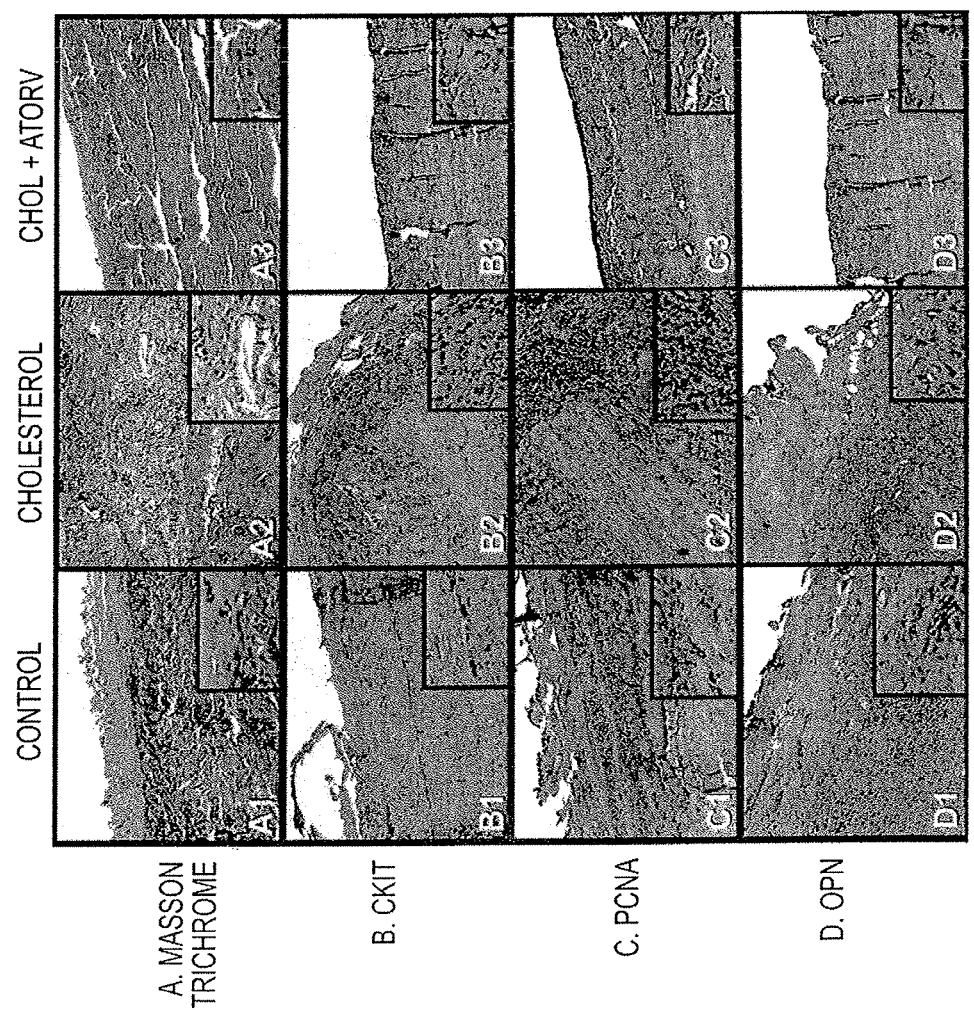
FIG. 4 depicts light microscopy slides of implanted valves from the three rabbit treatment groups with the left column, control diet; middle column, cholesterol diet; and right column, cholesterol diet plus atorvastatin. (All frames 20× magnification, with a 100× magnification in the right hand lower corner) Panel A. Masson Trichrome stain. Panel C. Proliferating cell nuclear antigen stain. Panel D. Osteopontin stain.

The implanted valve leaflets from the control animals appeared to have a mild amount of cellular infiltration along the surface of the leaflet as demonstrated by Masson Trichrome stain FIG. 4, Panel A1. The high power magnification demonstrates the demarcation between the leaflet and cellular infiltrate that develops along the leaflet surface. There was a small amount of cKit positive staining cells in control bioprosthetic valves FIG. 4, Panel B1, as well as a mild amount of proliferating cells expressing osteopontin, as shown in FIG. 4, Panels C1 and D1. In contrast, in the valve tissue from the cholesterol-fed rabbits FIG. 4, Panels A2, B2, C2, D2, there was marked cellular inflammatory infiltrate as shown in the Masson Trichrome, the cellular infiltrate express cKit, PCNA and OPN as shown in the high resolution field in the bottom left hand corner, with the blue staining cells. Finally, as measured by semi-quantitative visual analysis, at the time of explant and under the light microscopy, the atherosclerotic burden increased four-fold with the cholesterol treatment. The implanted leaflets in the atorvastatin treated rabbits demonstrated a marked decrease in the amount of atherosclerotic cellular infiltrate, proliferation, cKit and osteopontin expression FIG. 4, Panels A3, B3, C3, D3. The immunohistochemistry and Masson Trichrome demonstrate a dramatic improvement in the leaflets of the atorvastatin treated animals compared to the leaflets in the cholesterol-fed and control animals. Morphometric analysis demonstrated a 4-fold increase in the atherosclerotic burden as compared to the atorvastatin treated valves which attenuated the atherosclerosis significantly ($p<0.05$), the control had a 2-fold increase in inflammation secondary to the effect of implanting the valve in the rabbit inducing an inflammatory response.

Figure 5:
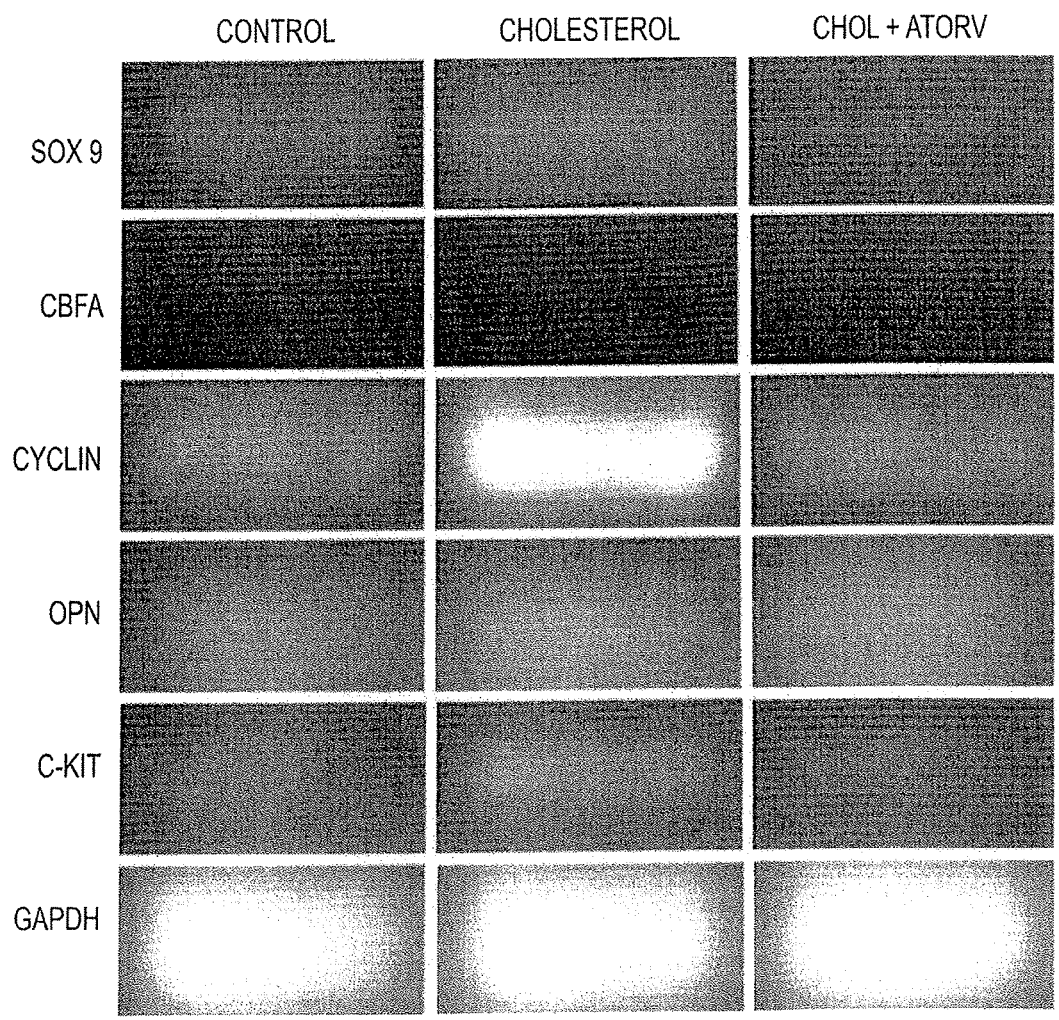
FIG. 5 depicts the Semi-Quantitative RT-PCR of the implanted valves from the three rabbit treatment groups; RT-PCR using the total RNA from the bioprosthetic valves for cKit (731 bp), Cyclin (151 bp), Osteopontin (OP) (102 bp), Sox9 (170 bp), Cbfa-1 (289 bp), and GAPDH (451 bp).

FIG. 5, demonstrates the RNA gene expression for the control, cholesterol and cholesterol plus atorvastatin treated rabbits. There was an increase in the Sox9 osteoblast transcription factor, Cyclin, and cKit in the leaflets of the cholesterol-fed animals as compared to the control with Cyclin and cKit significantly increased in the cholesterol over control ($p<0.05$) with atorvastatin attenuating cKit, Cyclin and Sox9 as compared to the cholesterol group ($p<0.05$). There was no expression of Cbfa1 and no difference in the osteopontin gene expression in all three different treatment groups. FIG. 7, is the RTPCR data from the rabbit study.

The serum cholesterol levels were significantly higher in the cholesterol fed compared to control animals (1846.0±525.3 mg/dL vs. 18.0±7 mg/dL, $p<0.05$). Atorvastatin treated rabbits manifested lower cholesterol levels than the rabbits receiving the cholesterol diet alone (824.0±152.1 mg/dl, $p<0.05$). There was an increase in hsCRP serum levels in the cholesterol fed compared to control rabbits (13.6±19.7 mg/dl vs. 0.24±0.1 mg/dL, $p<0.05$), which was reduced by atorvastatin (7.8±8.7 mg/dL, $p<0.05$) as per FIG. 7.

Recent epidemiological studies have revealed that the risk factors for bioprosthetic valve calcification, namely male gender, smoking, and elevated serum cholesterol, are similar to the risk factors associated with vascular atherosclerosis. This data demonstrate that experimental hypercholesterolemia produces biochemical and morphologic evidence of atherosclerotic changes along the surface of bioprosthetic pericardial valve tissue that are similar to the changes found in the early stages of aortic valve disease.

Specifically, there is an atherosclerotic lesion along the valve surface of animals fed a high-cholesterol diet, and attenuation of this process with atorvastatin. In this model, the hypercholesterolemic bioprosthetic valve not only developed an atherosclerotic lesion that is proliferative, but a lesion that expresses increased levels of bone matrix proteins, by immunohistochemistry and osteoblast bone marker, Sox9. The hsCRP levels are also increased in this model of experimental hypercholesterolemia, indicating an inflammatory environment for the homing of mesenchymal stem cells to the implanted leaflets. In the rabbit subcutaneous model, confirmation of an increase in Sox9 expression in bioprosthetic tissue removed from the hypercholesterolemic rabbits with associated atherosclerosis.

The finding of cKit and other mesenchymal expression, in these atherosclerotic bioprosthetic valves provides a mechanism, by which calcification can develop as shown in the mechanism. Referring to FIG. 6, the mechanism for bioprosthetic valve calcification is illustrated. In the presence of elevated cholesterol, hypertension, smoking, diabetes, and/or the process of abnormal oxidative stress, circulating stem cells home to a normal bioprosthetic heart valve and attach to the valve leaflet in the presence of cellular inflammation. The inflammation causes the circulating cKit positive cells, any and all types of osteogenic precursor cells, mesenchymal cells, seal positive cells, to attach to the ventricular and aortic surface causing calcification on both sides of the valve leaflet and/or stent and/or sewing ring. In the presence of risk factors, primarily hyperlipidemia which causes abnormal oxidative stress and abnormal endothelial nitric oxide synthase function in the newly formed endothelial lining cells lining around the implanted heart valve. The circulating cKit positive cells, circulating osteogenic precursor cells, mesenchymal cells, seal positive cells, "stick" to the newly formed endothelial lining along the implanted valve. These various types of stem cells have the ability to differentiate along the osteogenic pathway to form bone on the valve leaflet causing bioprosthetic valve leaflet deterioration. This differentiation process or a cell transformation process from one cell type to another occurs once Wnt is secreted from the newly formed endothelial lining cell, which surrounds the implanted valve. As the stem cells stick onto the newly formed endothelial lining in the presence of elevated lipids, and the close proximity of the stem cells sticking to the endothelial lining allows for the secreted Wnt to bind to the Lrp5 receptor which is located on the cell membrane of the "attached stem cell." Once the Lrp5/Wnt bind then the stem cell differentiates or transforms to a bone forming cell. An example of a compound to stop the cells from attaching to the valve, is the use of Atorvastatin as tested in the animal model to reduce inflammation to reduce the number of stem cells attaching to the valve leaflet, and slow the progression of the calcification. In the presence of hypercholesterolemia, cKit positive cells attach to the bioprosthetic valve and start to differentiate via an osteogenic gene program, first Sox9 upregulation in the low pressure model of the subcutaneous implant in vivo and then, Cbfa1 upregulation in the high pressure model of the ex vivo human explanted valves from surgery. The rest of the cells are native myofibroblasts differentiating into an osteoblast phenotype as implicated in other studies of aortic valve disease. In this model, as the environment of hypercholesterolemia induces inflammation, mesenchymal stem cells mobilize and home to the implanted bioprosthetic valve. These cells have the potential to differentiate along the osteogenic pathway as indicated in previous studies.

The foregoing findings demonstrate in an in vivo experimental model that hypercholesterolemia expresses cKit positive cells, atherosclerosis, and the osteogenic gene expression in pericardial bioprosthetic valve leaflets that may be a critical mechanism in bioprosthetic valve calcification.

To address the foregoing mechanism of valve calcification, the present inventor has invented a way to inhibit the stenosis, obstruction and/or calcification of the valves by inhibiting (i) three stages of bone formation, i.e. proliferation of circulating ckit and Seal positive stem cells, osteogenic cells, and mesenchymal stem cells in areas external and proximate to the bioprosthetic or mechanical valve, preventing extracellular matrix production of cartilage specific proteins, and osteoblastogenesis or deposition of bone matrix into the cartilage scaffold; and (ii) the attachment of the foregoing cells to the heart valve and/or Gortex lining on mechanical heart valves. The foregoing prevention is accomplished by activating nitric oxide in the endothelial cells themselves.

To activate nitric oxide in the endothelial cells, the heart valve leaflets are coated, post-fixation with glutaraldehyde, with a coating composition including one or more therapeutic agents, which adhere to the heart valve leaflets, stent and/or Gortex in the case of a mechanical heart valve. The coating composition may be deposited on both sides of the valve leaflets, the stent and/or sewing ring to which the bioprosthetic valve is secured, or the Gortex lining covering the sewing ring in the case of a mechanical valve, thereby inhibiting stenosis, obstruction, or calcification of the valve prosthesis following implantation in a patient in need thereof.

The coating compositions may be prepared by dissolving or suspending a polymer and therapeutic agent in a solvent. Suitable solvents that may be used to prepare the coating compositions include those that may dissolve or suspend the polymer and therapeutic agent in solution. Examples of suitable solvents include, but are not limited to, tetrahydrofuran, methylethylketone (MEK), chloroform, toluene, acetone, isooctane, 1,1,1, trichloroethane, dichloromethane, isopropanol, and mixtures thereof. However, solvents are not required in many cases.

The coating compositions may be applied by any method to the surface of the elastical stent portion of the valve prosthesis or bioprostheses and sewing ring, known by one skilled in the art. Suitable methods for applying the coating compositions to the surface of the elastical stent portion of the valve prosthesis include, but are not limited to, spray-coating, painting, rolling, electrostatic deposition, ink jet coating, and a batch process such as air suspension, pan-coating or ultrasonic mist spraying, or a combination thereof.

After the coating composition has been applied, it may be cured. As used herein, "curing" may refer to the process of converting any polymeric material into the finished or useful state by the application of heat, vacuum, and/or chemical agents, which application induces physico-chemical changes. The applicable time and temperature for curing are determined by the particular polymer involved and particular therapeutic agent used as known by one skilled in the art. Also, after the elastical stent is coated, it may be sterilized by methods of sterilization as known in the art (see, e.g., Guidance for Industry and FDA Staff—Non-Clinical Engineering Tests and Recommended Labeling for Intravascular Stents and Associated Delivery Systems http://www.fda.gov/medicaldevices/deviceregulationandguidance/guidancedocuments/ucm071863.htm and U.S. Pat. No. 7,998,404 entitled "Reduced temperature sterilization of stents."

The coating composition may include from one to four categories of therapeutic agents. The first category may be an eNOS activator; the second category an anti-proliferative agent to inhibit cell proliferation; the third category inhibits extracellular matrix production; and the fourth category inhibits the osteoblastogenesis.

To inhibit the attachment of the stem cells onto the "sticky" valve structure the goal is to upregulate the endothelial nitric oxide in the newly grown endothelial lining on the valve structure and in the circulating stem cells to prevent attachment of the stem cells to the valve structure. Agents that upregulate the production of nitric oxide (eNOS activators) may be selected from Atorvastatin, Rosuvastatin, Pravastatin, Mevastatin, Fluvastatin, Simvastatin, Lovastatin, L-Arginine, citrulline, NADPH, acetylcholine, histamine, arginine vasopressin, norepinephrine, epinephrine, bradykinin, adenosine di,triphosphate, 5-Hydroxytrptamine, thrombin, insulin, glucocorticoids, salicylates, L-NMMA, L-NAME, nitroglycerine, isosorbide dinitrate, isosorbide 5-mononitrate, amyl nitrite, nicorandil, tetrahydrobiopterin and combinations of the foregoing.

In addition, agents that upregulate nitric oxide and lipid lowering drugs may be given orally in varying dosages depending on a patient's weight. Such agents include Atorvastatin (10 to 80 mg per day depending on the LDL levels in the patient), Rosuvastatin (5-40 mg a day), Pravastatin (10-40 mg a day), Mevastatin (5-40 mg a day), Fluvastatin (5-40 mg a day), Simvastatin (5-40 mg a day), Lovastatin (5-40 mg a day), Zetia (10 mg a day) and combinations of the foregoing.

A PCSK9 inhibitor may be given by intramuscular injection to the patient in a dosage that correlates with the patient's weight. The initial dose of a PCSK9 inhibitor may be about 0.25 mg/kg, about 0.5 mg/kg, about 1 mg/kg or about 1.5 mg/kg, and the initial dose and the first subsequent dose and additional subsequent doses may be separated from each other in time by about one week. PCSK9 inhibitors and their dosages include Alirocumab in an amount of from 75-150 mg every 2 to 4 weeks and Evolocumab 140 mg every 2 weeks, may be given by subcutaneous injection, bimonthly or monthly and combinations of the foregoing. PCSK9 is a regulator of plasma lipoprotein cholesterol (LDL-C) and an agent that is effective in risk reduction in coronary artery disease. The proprotein convertase subtilisin/kexin type 9 (PCSK9) protein regulates the activity of low-density lipoprotein (LDL) receptors, which are located along the endothelium and in the liver of the patient. Inhibition of PCSK9 with a monoclonal antibody results in increased cycling of LDL receptors and increased clearance of LDL cholesterol (LDL-C). Highly expressed in the liver, PCSK9 is secreted after the autocatalytic cleavage of the prodomain, which remains non-covalently associated with the catalytic domain. The catalytic domain of PCSK9 binds to the epidermal growth factor-like repeat A (EGF-A) domain of low density lipoprotein receptor (LDLR). Both functionalities of PCSK9 are required for targeting the LDLR-PCSK9 complex for lysosomal degradation and lowering LDL-C, which is in agreement with mutations in both domains linked to loss-of-function and gain-of-function.

Atorvastatin may be given orally in the range of 10 mg to 80 mg, Simvastatin in the range of 10 mg to 40 mg, Rosuvastatin 5 mg to 40 mg, Pravastatin 10 mg to 80 mg, Pitavastatin 1 mg to 4 mg.

It is equally important to include in the coating composition therapeutic agents that that inhibit the three stages of osteogenic bone formation. Agents selected from paclitaxel, sirolimus, biolimus, everolimus, tacrolimus and combinations of the foregoing may be included in the coating composition to inhibit cell proliferation.

The coating composition may also include inhibitors of extracellular matrix production such as an anti-farnysltransferase inhibitor (FTI) and an anti-palmitoylation inhibitor. Such agents may include Lonafarnib, Zarnestra R115777, FTI SCH66336, STI571, FLT-3 Inhibitor, Proteasome Inhibitor, MAPK Inhibitor, BMS-214662, Type I non-lipid inhibitors of protein palmitoylation, farnesyl-peptide palmitoylation or Type 2 inhibitors myristoyl-peptide palmitoylation, palmitoylation acyltransferase inhibitors, lipid based palmitoylation inhibitors including 2-bromopalmitoyl (2BP), tunicamycin, cerulnin and combinations of the foregoing.

FTI inhibitors anti-palmitoylation inhibitors may also be given orally. Lonafarnib may be given in a dosage of 115 mg/m2 dose with a range from 115 mg/m2 to 150 mg/m2, in combination with an effective amount of Zetia of 10 mg.

The coating composition may also include anti-osteoporotic agents such as bisphosphonate drugs including Alendronate (5-70 mg orally depending on the patient's clinical status), Risedronate (5-150 mg orally a day depending on the patient's clinical status), Zoledronic acid (5 mg IV infusion over 15 min once a year), Etidronate (20 mg/kg per day for one month after placement of the valve), Ibandronate (150 mg orally once a month), Pamidronate (60-90 IV infusion one time dose), Tiludronate (400 mg orally once a day for 3 months), Denosumab antibody (60 mg subcutaneous injection every 6 months), Calcitonin-Calcimare (60 mg orally each day), Miacalcin (60 mg orally each day), Forteo Teriparatide (60 mg orally each day), Raloxfine (Evista) (60 mg orally each day) and combinations of the foregoing. These agents will inhibit the final bone formation stage by inhibiting bone formation in the implanted valve.

The foregoing agents that treat the third phase of bone formation may also be given to the patient orally or by intramuscular injection in a dosages that corresponds with the patient's weight.

EXAMPLE I

A bioprosthetic heart valve is coated with a coating composition including an eNOS activator, Atorvastatin, an anti-proliferative agent, paclitaxel; an inhibitor of extracellular production, an anti-farnysltrasferase inhibitor; and an inhibitor of osteoblastogenesis, a bisphosphonate drug. The bioprosthetic heart valve is implanted in a 75 year old female patient. The patient also receives lipid lowering therapy including atorvastatin 80 mg by mouth each day and a PCSK9 inhibitor once a month in an amount of 75 mg by subcutaneous injection to lower her LDL cholesterol level from 350 mg/ml to 80 mg/ml. On review of her echocardiogram the leaflets and stent of the implanted bioprosthetic valve have normal hemodynamics over a 25 year period with a mean gradient of 10 mm Hg and an Aortic Valve area of 2.0 cm2. The bioprosthetic valve leaflets and stent do not exhibit any evidence of calcification as diagnosed by Computed tomography and echocardiography.

Although the present invention has been described with reference to various aspects and embodiments, those of ordinary skill in the art will recognize that changes may be made in form and detail without departing from the spirit and scope of the invention.

I claim:

1. An apparatus for inhibiting stenosis, obstruction and/or calcification of a heart valve following implantation in a vessel having a wall comprising:
   a fixative-pretreated bioprosthetic heart valve having one or more cusps, said fixative-pretreated bioprosthetic heart valve mounted on an elastical stent for replacement of a natural diseased valve;
   a coating composition coated on said one or more cusps of the bioprosthetic heart valve after fixation thereof, on said stent or both, wherein said coating composition includes an eNOS activator; an anti-proliferative agent for inhibiting cell proliferation; an extracellular matrix production inhibitor; and an inhibitor of osteoblastogenesis,
   wherein said coating composition when eluted inhibits stenosis, obstruction and/or calcification of the bioprosthetic heart valve when implanted by preventing the attachment of cKit positive stem cells, SCA1 cells, COP cells, and/or mesenchymal stem cells to the bioprosthetic heart valve by activating nitric oxide production (i) in the circulating stem cells, (ii) in an endothelial cell lining covering the bioprosthetic heart valve tissue, (iii) or both.

2. The apparatus of claim 1 wherein the eNOS activator is selected from Atorvastatin, Rosuvastatin, Pravastatin, Mevastatin, Fluvastatin, Simvastatin, Lovastatin, L-Arginine, citrulline, NADPH, acetylcholine, histamine, arginine vasopressin, norepinephrine, epinephrine, bradykinin, adenosine di,triphosphate, 5-Hydroxytrptamine, thrombin, insulin, glucocorticoids, salicylates, L-NMMA, L-NAME, nitroglycerine, isosorbide dinitrate, isosorbide 5-mononitrate, amyl nitrite, nicorandil, tetrahydrobiopterin, Zetia and combinations of the foregoing.

3. The apparatus of claim 1 wherein said anti-proliferative agent is selected from paclitaxel, sirolimus, biolimus, everolimus and combinations of the foregoing.

4. The apparatus of claim 1 wherein said inhibitor of extracellular production is selected from an anti-farnysltransferase inhibitor, an anti-palmitoylation inhibitor or both.

5. The apparatus of claim 4 wherein said anti-farnysltransferase inhibitor and said anti-palmitoylation inhibitor are selected from Lonafarnib, Zarnestra R115777, FTI SCH66336, STI571, FLT-3 Inhibitor, Proteasome Inhibitor, MAPK Inhibitor, BMS-214662, Type I non-lipid inhibitors of protein palmitoylation, farnesyl-peptide palmitoylation or Type 2 inhibitors myristoyl-peptide palmitoylation, palmitoylation acyltransferase inhibitors, lipid based palmitoylation inhibitors including 2-bromopalmitoyl (2BP), tunicamycin, cerulnin and combinations of the foregoing.

6. The apparatus of claim 1 wherein said inhibitor of osteoblastogenesis is selected from anti-osteoporotic agents such as bisphosphonate drugs including Alendronate, Risedronate, Zoledronic acid, Etidronate, Ibandronate, Pamidronate, Tiludronate, Denosumab antibody, Calcitonin-Calcimare, Miacalcin, Forteo teriparatide, raloxfine (Evista) and combinations of the foregoing.

* * * * *